US005674988A

United States Patent [19]
Sabesan

[11] Patent Number: 5,674,988
[45] Date of Patent: Oct. 7, 1997

[54] 4-N-SUBSTITUTED SIALIC ACIDS AND THEIR SIALOSIDES

[75] Inventor: Subramamiam Sabesan, Wilmington, Del.

[73] Assignee: E. I. Du Pont de Nemours and Company, Wilmington, Del.

[21] Appl. No.: 594,422

[22] Filed: Jan. 31, 1996

Related U.S. Application Data

[63] Continuation of Ser. No. 201,917, Feb. 25, 1994, abandoned.
[51] Int. Cl.[6] .................................................. C07H 17/00
[52] U.S. Cl. ...................... 536/17.9; 536/18.5; 536/55.3; 514/23
[58] Field of Search ................... 536/17.9, 18.5, 536/55.3; 514/23

[56] References Cited

U.S. PATENT DOCUMENTS

| 5,220,008 | 6/1993 | Sabesan et al. | 536/4.1 |
|---|---|---|---|
| 5,243,035 | 9/1993 | Nakabayashi et al. | 536/4.1 |

FOREIGN PATENT DOCUMENTS

| 2062406 | 9/1992 | Canada | C07H 5/06 |
|---|---|---|---|
| WO 91/09972 | 7/1991 | WIPO | C12Q 1/34 |
| WO 92/06691 | 4/1992 | WIPO | A61K 31/70 |

OTHER PUBLICATIONS

Ogura, H., et al, Tetrahedron Let. 22(43), 4265–4268, 1981.
Zbiral, E. et al, carbohydrate Res., 194, C15–C18 (1989).
Hasegawa, A. et al, Carbohydrate Res., 230, 257–272 (1992).
Baumberger, F. et al, Helvetica Chimica Acta, 69, 1927–1935 (1986).
Hagedorn, H.W. et al, Helvetica Chimica Acta, 69, 2127–2132 (1986).
Knibbs, R.N. et al, J. of Biological Chemistry, 268(25), 18524–18531 (1993).
Schreiner, E. et al, Liebigs Ann. Chem., pp. 129–134 (1991).
Estenne, G. et al, J. Carbohydrate Chem., 10(2), 181–195 (1991).
Suzuki et al, Glycoconjugate, 7, 349–356, 1990.
Sabesan et al, Carbohydr. Res., 218, 27–54, 1991.
Pritchett et al, Virology, 160, 502–506, 1987.
Pritchett et al, J. Biol. Chem., 264, 9850–9859, 1989.
Baumberger, F. et al, Helvetica Chimica Acta., 71, 429–445, 1988.
Air et al, J. Virol., 64(12), 5797–5803, 1990.
Nagai et al, Chem. Pharm. Bull., 38(5), 1329–1332, 1990.
Burnet, F.M. et al, Aust. J. Exp. Biol. Med. Sci., 25, 227–233, 1947.
Stone, J.D., Aust. J. Exp. Biol. Med. Sci., 26, 48–64, 1948.
von Itzstein, M. et al, Nature, 363(6428), 418–423, 1993.
von Itzstein, M. et al, Carbohydrate Research, 244, 181–185, 1993.
Baumberger, F. et al, Helvetica Chimica Acta, 69, 1535–1541, 1986.
Schreiner, et al, Liebigs. Ann. Chem., 129–134, 1991.

*Primary Examiner*—John W. Rollins

[57] ABSTRACT

Novel azide groups containing sialosides and a process for their preparation is provided. The methods and resulting compounds may be of pharmaceutical interest for the inhibition of the influenza virus neuraminidase.

7 Claims, 2 Drawing Sheets

4-N-SUBSTITUTED SIALIC ACIDS AND THEIR SIALOSIDES

This is a continuation, division of application Ser. No. 08/201,917 filed Feb. 25, 1994, now abandoned.

FIELD OF THE INVENTION

Sialic acids are a group of acidic 9 carbon-keto-sugars found glycosidically linked to other sugars in glycoproteins and glycolipids which serve as receptor determinants for viruses, toxins, adhesion proteins, antibodies and lectins. The design of synthetic sialosides and their analogs is of pharmaceutical interest. This invention provides novel azide, amino and acylamino group containing sialosides, a process for their preparation, and a method for their use in inhibiting influenza sialidase activity.

TECHNICAL BACKGROUND

Sialidases are enzymes present on viral protein coats and bacterial outer membranes. They serve to process the carbohydrate moieties of glycoproteins and glycolipids terminated with sialic acids that are found on host cell surfaces. The processing of these glycoprotein and glycolipid moieties are crucial in the pathogen replication cycle. A specific example of this particular host-pathogen species is the influenza virus and the erythrocyte. Influenza virus binds to the erythrocytes through attachment to cell surface carbohydrates. Specifically, the virus has a membrane envelope with two types of surface glycoproteins, the hemagglutinin and the neuraminidase (sialidase), both of which interact with sialyloligosaccharides on host (erythrocyte) cells. It has long been known that pretreatment of erythrocytes or host cells with bacterial sialidase abolishes viral adsorption and/or infection, demonstrating that sialic acid is an essential feature of the receptor determinant (Burnet, F. M. and Stone, J. D., Aust. J. Exp. Biol. Med. Sci., 25, 227–233 (1947) and Stone, J. D., Aust. J. Exp. Biol. Med. Sci., 26, 48–64 (1948)). Hemagglutinin attaches to the host cell structure which contains sialic acid, galactose and N-acetylglucosamine. Neuraminidase functions to hydrolyze the sialic acid from receptors, and at high pathogen levels in an infected cell this neuraminidase activity aids in elution of the budding virus from the host membrane, thus facilitating replication of the pathogen.

The 4-amino- and -guanidino-2,3-dehydrosialic acids have recently been shown to be extremely potent inhibitors of the influenza virus neuraminidase and may become useful as an anti viral drug. The high binding potencies of these unnatural compounds have been shown to arise from the electrostatic interaction between the 4-amino or guanidino groups of the dehydrosialic acids and the carboxyl residues at the active site of the neuraminidase. Such interaction should also be possible in ketosidically linked sialosides that represent the terminal carbohydrate structures of glycoproteins and glycolipids (M. von Itzstein et al., Nature, 418–423 (1993)).

M. von Itzstein et al., Carbohydrate Research, 244: 181–185 (1993) disclose a method for the preparation of methyl (5-acetamido-7,8,9-tri-O-acetyl-2,6-anhydro-4-azido-3,4,5-trideoxy-D-glycero-D-galacto-non-2-en)onate (3). There is no disclosure nor suggestions concerning any further reactions of this compound.

SUMMARY OF THE INVENTION

This invention provides a process for the hydrochlorination of 4-azido-2,3-dehydrosialic acids or 4-deoxy-2,3-dehydrosialic acids (I) to the corresponding 4-azido-2-chlorosialic acids or 4-deoxy-2-chlorosialic acids (II) according to the equation

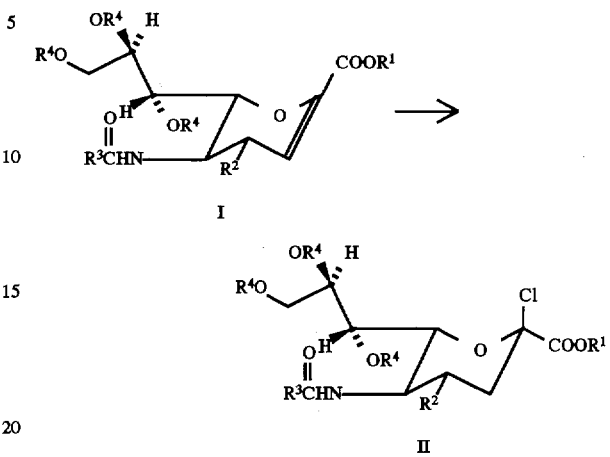

where
$R^1$ is $C_1$ to $C_{20}$ alkyl,
$R^2$ is azido or hydrogen,
$R^3$ is H or a $C_1$ to $C_{20}$ hydrocarbyl or substituted hydrocarbyl, and
$R^4$ is acyl containing from 1 to 8 carbon atoms, or a $C_1$ to $C_{20}$ alkyl,
which process comprises contacting under reactive conditions the 4-azido-2,3-dehydrosialic acid or 4-deoxy-2,3-dehydrosialic acid with anhydrous hydrogen chloride in the presence of a polar aprotic solvent or a organic carboxylic acid solvent. This process is further enhanced by the presence of lithium chloride.

This invention further provides the 4-azido-2-chlorosialic acids or 4-deoxy-2-chlorosialic acids of the structure II.

This invention further provides compounds of the structure III

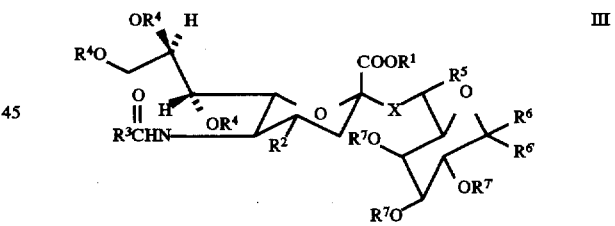

where
X is oxygen, sulfur, $CR^9R^{10}$, or $NR^{11}$;
$R^1$ is H, $C_1$–$C_{20}$ alkyl, a mono, di or polyvalent cation of an alkali metal, alkaline earth metal or transition metal, or an ammonium or substituted ammonium ion;
$R^2$ is azido, acylamino, where the acyl group contains from 1 to 8 carbon atoms, amino, hydrogen or guanidino;
$R^3$ is H or a $C_1$ to $C_{20}$ hydrocarbyl or substituted hydrocarbyl;
$R^4$ is H, acyl containing from 1 to 8 carbon carbon atoms, or a $C_1$ to $C_{20}$ alkyl;
$R^5$ is H, a $C_1$ to $C_{20}$ hydrocarbyl or substituted hydrocarbyl;
$R^6$ and $R^{6'}$ are H, OH, a $C_1$ to $C_{20}$ alkoxy or substituted alkoxy, a mono, di or oligosaccharide, or an alkylideneoxy taken together with $R^{7'}$ when $R^{7'}$ is not H;

provided that one of $R^6$ and $R^{6'}$ must be H but $R^6$ and $R^{6'}$ may not both be H; and $R^7$ and $R^{7'}$ are H, acyl containing from 1 to 8 carbon atoms, or a $C_1$ to $C_{20}$ alkyl, aryl, or alkylidene taken together with an adjacent $R^6$, $R^{6'}$ $R^7$ or $R^{7'}$;

where $R^9$, $R^{10}$ and $R^{11}$ are independently H or a $C_1$–$C_{20}$ hydrocarbyl or substituted hydrocarbyl.

This invention further provides compounds of the structure IV

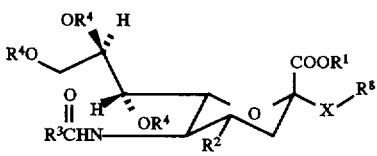

where $R^1$ is H, $C_1$–$C_{20}$ alkyl, a mono, di or polyvalent cation of an alkali metal, alkaline earth metal or transition metal, or an ammonium or substituted ammonium ion;

$R^2$ is azido, acylamino, where the acyl group contains from 1 to 8 carbon atoms, amino, guanidino or hydrogen; and $R^3$ is H or $C_1$ to $C_{20}$ hydrocarbyl or substituted hydrocarbyl;

$R^4$ is H, acyl containing from 1 to 8 carbon atoms or a $C_1$ to $C_{20}$ alkyl;

$R^8$ is $C_1$ to $C_{20}$ hydrocarbyl or substituted hydrocarbyl, acyl containing from 1 to 8 carbon atoms;

$R^9$, $R^{10}$, and $R^{11}$ are independently H or a $C_1$–$C_{20}$ hydrocarbyl or substituted hydrocarbyl;

X is oxygen, sulfur, $CR^9R^{10}$ or $NR^{11}$.

This invention further provides a method for inhibiting sialidase activity comprising contacting sialidase with a compound of the formula III

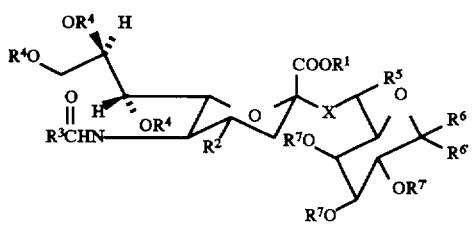

where

X is oxygen, sulfur, $CR^9R^{10}$, or $NR^{11}$;

$R^1$ is H, a mono, di or polyvalent cation of an alkali metal, alkaline earth metal or transition metal, or an ammonium or substituted ammonium ion;

$R^2$ is amino or guanidino;

$R^3$ is H or $C_1$ to $C_{20}$ hydrocarbyl or substituted hydrocarbyl;

$R^4$ is H;

$R^5$ is H, a $C_1$ to $C_{20}$ hydrocarbyl or substituted hydrocarbyl;

$R^6$ and $R^{6'}$ are H, OH, a $C_1$ to $C_{20}$ alkoxy or substituted alkoxy, a mono, di or oligosaccharide, or an alkylideneoxy taken together with $R^{7'}$ when $R^{7'}$ is not H; provided that one of $R^6$ and $R^{6'}$ must be H but $R^6$ and $R^{6'}$ may not both be H; and $R^7$ and $R^{7'}$ are H or alkylidene taken together with an adjacent $R^6$, $R^{6'}$, $R^7$ or $R^{7'}$ where $R^9$, $R^{10}$ and $R^{11}$ are independently H or a $C_1$–$C_{20}$ hydrocarbyl or substituted hydrocarbyl.

This invention further provides compounds of the formula III

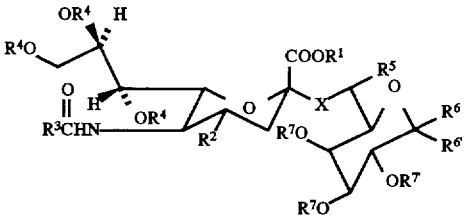

where

X is oxygen, sulfur, $CR^9R^{10}$, or $NR^{11}$;

$R^1$ is H, $C_1$–$C_{20}$ alkyl, a mono, di or polyvalent cation of an alkali metal, alkaline earth metal or transition metal, or an ammonium or substituted ammonium ion;

$R^2$ is amino or a guanidino;

$R^3$ is H or $C_1$ to $C_{20}$ hydrocarbyl or substituted hydrocarbyl;

$R^4$ is H;

$R^5$ is a H, $C_1$ to $C_{20}$ hydrocarbyl or substituted hydrocarbyl;

$R^6$ and $R^{6'}$ are H, OH, a $C_1$ to $C_{20}$ alkoxy or substituted alkoxy, a mono, di or oligosaccharide, or an alkylideneoxy taken together with $R^{7'}$ when $R^{7'}$ is not H; provided that one of $R^6$ and $R^{6'}$ must be H but $R^6$ and $R^{6'}$ may not both be H; and $R^7$ and $R^{7'}$ are H or alkylidene taken together with an adjacent $R^6$, $R^{6'}$, $R^7$ or $R^{7'}$;

where $R^9$, $R^{10}$ and $R^{11}$ are independently H or a $C_1$–$C_{20}$ hydrocarbyl or substituted hydrocarbyl having sialidase resistance.

BRIEF DESCRIPTION OF THE DRAWINGS

FIG. 1 shows the chemical structures of compounds prepared in the examples.

FIG. 2A and 2B show inhibition to influenza neuraminidase hydrolysis of αDNeuAc2,6βDLacNAc by the 4-aminosialoside 12 FIG. 2A and by the 4-amino-thiosialoside 14 FIG. 2B.

DETAILED DESCRIPTION OF THE INVENTION

Applicant provides for (1) the first concise synthesis of 4-azido, amino and acetamido-substituted sialyl disaccharides; (2) the discovery that the azido or acetamido groups at the 4-position of sialic acids of O-linked sialosides imparts resistance to the hydrolytic action of the neuraminidase; and (3) the identification of potent 4-amino-sialoside and 4-amino-thiosialoside inhibitors for the influenza neuraminidase.

The starting materials for the process of the present invention are known compounds. For example, for methyl (5-acetamido-7,8,9-tri-O-acetyl-2,6-anhydro-4-azido-3,4,5-trideoxy-D-glycero-D-galacto-non-2-en)onate, a compound of generic structure I where $R^1$ is methyl, $R^2$ is azido, $R^3$ is methyl and $R^4$ is acetyl, the synthetic route starts from the known, commercially available, N-acetyl-neuraminic acid (1). This synthesis, carried out in experiments 1, 2 and 3, is illustrated in synthetic sequence 1.

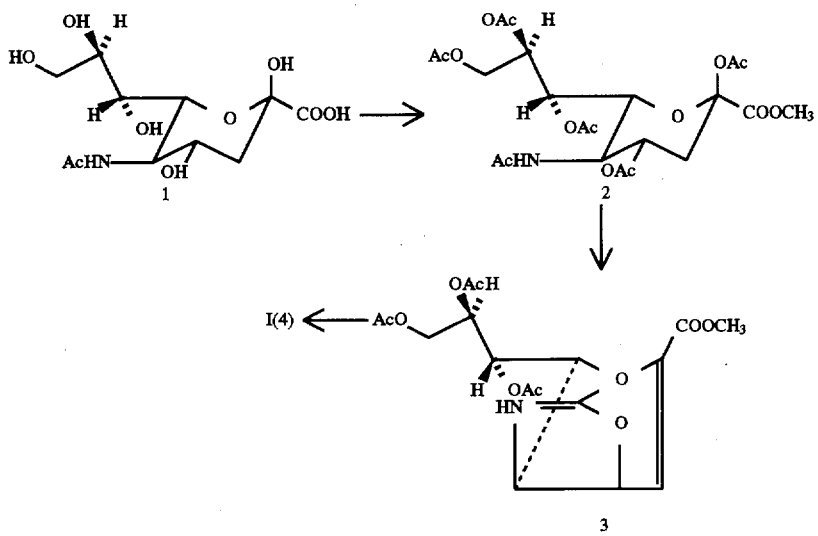

The process of the present invention is illustrated in Example 4 for the conversion of a compound of general structure I (specific compound 4, where, in I, $R^1$ is $CH_3$, $R^2$ is $N_3$, $R^3$ is $CH_3$, and $R^4$ is $CH_3CO$) to a compound of general structure II (specific compound 5, where, in II, $R^1$ is $CH_3$, $R^2$ is $N_3$, $R^3$ is $CH_3$, and $R^4$ is $CH_3CO$).

Figure 1:
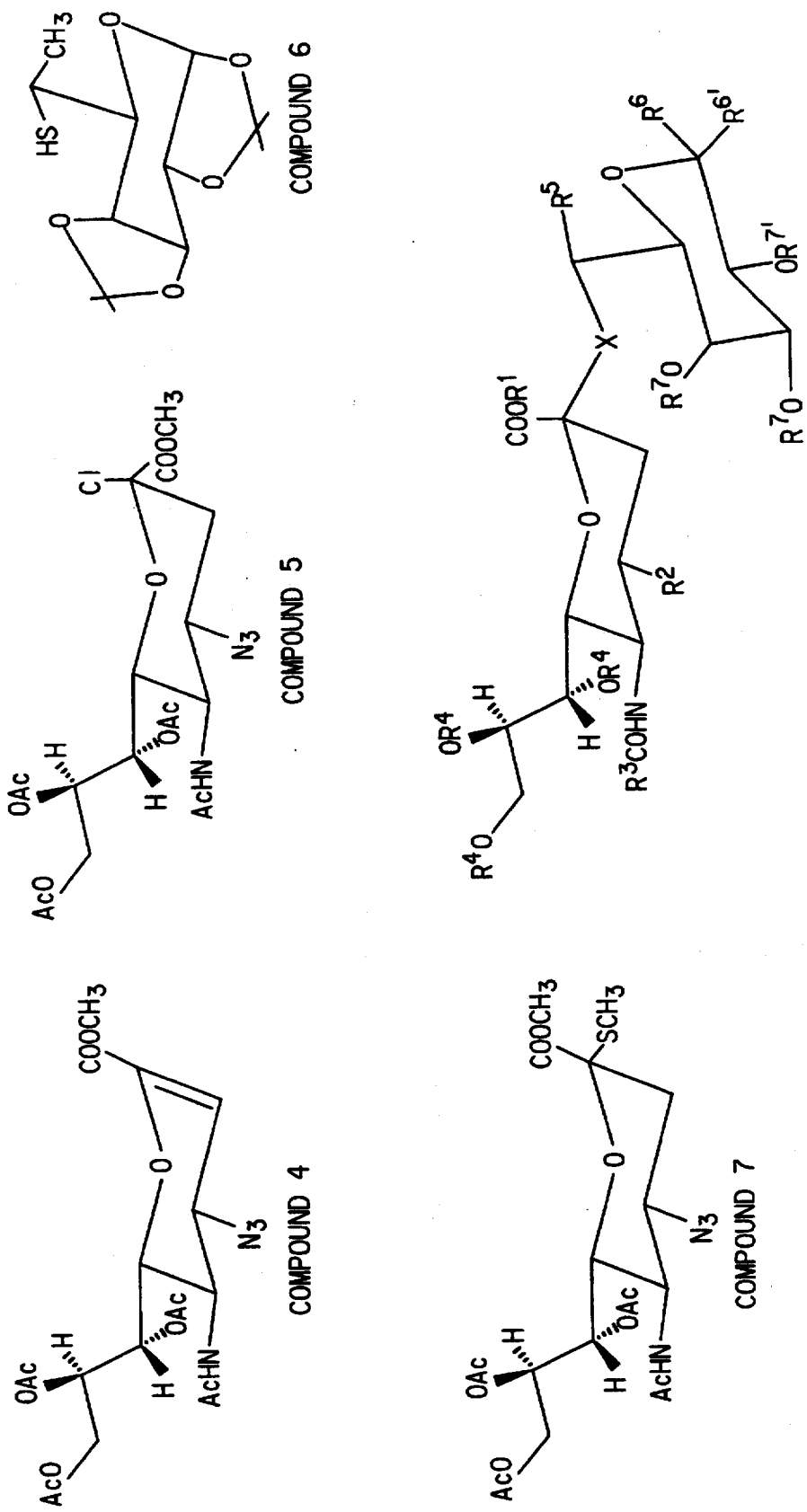

For the process of the present invention, i.e., the process for the conversion of compounds of the generic structure I to compounds of the generic structure II, a source of anhydrous hydrogen chloride is required. This may comprise anhydrous hydrogen chloride gas itself, or may involve the in situ dehydration of water-containing hydrochloric acid, for example by molecular sieves.

The process is carried out under substantially anhydrous conditions under an inert gas atmosphere, e.g., nitrogen or argon.

The process is carried out in a solvent, an aprotic organic solvent such as acetonitrile, dimethylformamide, dimethylacetamide, dimethylsulfoxide and halogenated organic solvents such as methylene chloride, chloroform and carbon tetrachloride or an organic carboxylic acid solvent such as acetic acid. Acetonitrile is preferred.

The process is generally conducted at 0° C. to 25° C. for extended periods of time, i.e., from 24 hours to six or more days.

Lithium chloride is an optional additive to the process reaction media. It serves to increase the concentration of chloride available for the reaction. Its presence is not required.

Conversion of the compounds II to the novel compounds III and IV is illustrated by Examples 6 to 14. Conversion of compound II to other type III compounds is carried out by methods known in the art. For example, to prepare III when X is $CR^9R^{10}$, Compound II is allowed to react with an appropriate carbanion. To prepare III when X is $NR^{11}$, compound II is allowed to react with an appropriate amine. The ester function can be hydrolyzed so that $R^1$ can be converted to H or various salts.

Compounds III and IV where $R^4$ is acyl or alkyl can be converted to compounds where $R^4$ is H by hydrolysis according to methods known in the art.

Compounds that are especially useful in the method for inhibiting sialidase activity are of generic structure III where X is S, $R^1$ is Na, $R^2$ is $NH_2$, $R^3$ is $CH_3$, $R^4$ is H, $R^5$ is $CH_3$, one of $R^6$ and $R^{6'}$ is OH, the other is H and $R^7$ and $R^{7'}$ is H or where X is O, $R^1$ is Na, $R^2$ is $NH_2$, $R^3$ is $CH_3$, $R^4$ is H, $R^5$ is H, one of $R^6$ and $R^{6'}$ is OH, the other is H and $R^7$ and $R^{7'}$0 is H. These are prepared in Examples 11 and 13.

Preferred compounds resistant to neuramidase hydrolysis activity are those of generic structure III where X is S, $R^1$ is Na, $R^2$ is H, azido or acetamido, $R^3$ is $CH_3$, $R^4$ is H, $R^5$ is $CH_3$, one of $R^6$ and $R^{6'}$ is OH, the other is H and $R^7$ is H.

Other preferred compounds resistant to neuramidase hydrolysis activity are those of generic structure III where X is O, $R^1$ is Na, $R^2$ is azido, $R^3$ is $CH_3$, $R^4$ is H, $R^5$ is H or $CH_3$, one of $R^6$ and $R^{6'}$ is OH, the other is H and $R^7$ is H.

Still other preferred compounds resistant to neuramidase hydrolysis activity are those of generic structure III where X is O, $R^1$ is Na, $R^2$ is acetamido, $R^3$ is $CH_3$, $R^4$ is H, $R^5$ is H, one of $R^6$ and $R^{6'}$ is OH, the other is H and $R^7$ is H and where X is O, $R^1$ is Na, $R^2$ is acetamido, $R^3$ is $CH_3$, $R^4$ is H, $R^5$ is $CH_3$, $R^6$ is 2-(trimethylsilyl)ethoxy, $R^{6'}$ is H, and $R^7$ is H.

FIG. 1 shows the chemical structures of compounds prepared in the examples. For the generic structure III, the substituent coding is as follows:

Compound 8 X=S, $R^1$=Me, $R^2$=$N_3$, $R^3$=Me, $R^4$=$CH_3CO$, $R^5$=Me, $R^6$=H, $R^{6'}$ is isopropylideneoxy taken together with $R^{7'}$ and both $R^{7'}$s= isopropylidene, Compound 9 as 8 except, X=O and $R^5$=H, Compound 10 X=O, $R^1$=Na, $R^2$=$N_3$, $R^3$=Me, $R^4$, $R^5$, one of $R^6$ and $R^{6'}$ is H, the other is OH, and $R^7$ and $R^{7'}$=H, Compound 11 as 10 except $R^2$=NHC(=O)$CH_3$, Compound 12 as 10 except $R^2$=$NH_2$, Compound 13 X=S, $R^1$=Na, $R^2$=$N_3$, $R^3$=Me, $R^4$=H, $R^5$=Me, one of $R^6$ and $R^{6'}$ is H, the other is OH, and $R^7$ and $R^{7'}$=H, Compound 14 as 13 except $R^2$=$NH_2$.

Inhibition of Neuraminidases by Thiosialosides

In order to determine the effectiveness of the instant thiosialosides as neuraminidase inhibitors, incubations were performed involving the neuraminidase, the thiosialoside inhibitor and a $^{14}$C-labeled substrate, $^{14}$C-labeled αDNeuAc (2-6) βDGal (1-4) DGlcNAc (A).

EXPERIMENT 1

Preparation of $^{14}$C-labelled

αDNeuAc(2-6) βDGal (1-4) DGlc (A)

The compound was made as described by Unversagt, C. et al., J. C., *J. Am. Chem. Soc.* 1990, 112, 9308–9309. $^{14}$C-Labeled N-acetyl-D-glucosamine ($^{14}$C-D-GlcNAc, 50 uCi, NEN, MA) was mixed with D-GlcNAc (13.5 mg, 61.1 mmole) and UDP-galactose (45.3 mg, 80 mmole), dissolved in a buffer (1.7 mL, pH 7.4) containing $MnCl_2$ (10 mmole), sodium cacodylate (50 mmole) and galactosyl transferase (5 U, EC. 2. 4. 1. 22, Sigma Chemical Company, St. Louis, Mo.), and incubated at 37° C. for 24 h. The reaction mixture was passed through a Dowex phosphate resin column (200–400 mesh) containing Chelex resin (500 mg) packed on the top. The column was eluted with deionized water (30 mL) and the eluant was concentrated to a dry residue, which was dissolved in 100 mM sodium cacodylate buffer (2.5 mL, pH 6.5) containing CMP-NeuAc (50 mg, Sigma Chemical Co.), bovine alkaline phosphatase (6 U), bovine serum albumin (5 mg) and Galβ1.4GlcNAc a 2,6 sialyl transferase (500 mU, E.C. 2.4.99.5), and incubated at 37° C. for 24 h. The reaction mixture was diluted with water to 12 mL and applied to a column of Dowex-phosphate resin (200–400 mesh) and eluted with water (75 mL). The elution buffer was then changed to 5 mM sodium phosphate buffer (pH 6.8) and fractions (7.5 mL) were collected. A sample of the fraction (10 μL) was diluted with scintillation liquid (3 mL, Formula 989, NEN, MA) and the radioactivity was measured. The products appeared in fractions 17–30. These were pooled and evaporated to a dry residue, redissolved in water and applied to a column of Sephadex G-15 (75 mL), equilibrated and eluted with deionized water. The fractions (2 mL) containing the radioactivity were pooled and lyophilized to obtain a colorless material (38 mg).

Inhibition constants of the inhibitors were determined by incubating (37° C.) a solution of A at four different concentrations with the neuraminidase, in the presence or absence of the inhibitors. After the reaction, the reaction mixture was diluted with deionized water and passed through a column of Dowex resin. The column was further eluted with deionized water. Under these conditions, only the free LacNAc elutes. The eluant was diluted with Scintillation fluid (10 mL, Formula 989, NEN, MA) and the radioactivity was measured, and the amount of free LacNAc liberated was determined.

EXAMPLES

GENERAL METHODS

Unless otherwise specified, all the reagents were purchased from Aldrich Chemical Co. (St. Louis, Mo.). Thin layer chromatography was performed on precoated plates of Silica Gel 60 $F_{254}$ (EM Science), and the spots were visualized with a spray containing 5% sulfuric acid in ethanol, followed by heating. Column chromatography was done on silica gel 60 (230–400 mesh, EM Science). $^1$H NMR spectra were recorded at 300, 500 or 600 MHz (GE Omega-300, GE Omega 500 or Bruker AM-500, AMX-600) and the $^{13}$C- NMR spectra were recorded with the above instruments operating at 75.48 or 125.74 MHz (300 and 500 MHz, respectively for proton). The hydrogen and carbon chemical shifts in organic solvents are expressed relative to tetramethylsilane (TMS). The hydrogen and carbon atoms are numbered from the reducing end units. For solutions of compounds in deuterium oxide or deuterated methanol, the hydrogen chemical shift values are expressed relative to the HOD signal (4.75 ppm at 296° K., internal acetone 2.23 ppm), and the carbon chemical shifts are expressed relative to external TMS using the deuterium lock of the spectrometer, which set the chemical shifts of 1,4-dioxane at 66.9 ppm.

For purposes of this subject matter, the following terms and abbreviations are used: "sec" means second(s), "min" means minute(s), "h" means hour(s), "d" means day(s), "mL" means milliliter, and "g" means gram(s).

EXAMPLE 1

Methyl (5-acetamido-3,5-dideoxy-2,4,7,8,9-penta-O-acetyl-β-D-glycero-D-galactononulopyranosyl)onate 2: Compound 2 was prepared according to the published methods (Baggett, N; Marsden, B. J. *Carbohydr. Res.* (1982) 110, 11–18; Hasegawa, A.; Ohki, H.; Nagahama, T.; Ishida, H.; Kiso, M. *Carbohydr. Res.* (1991) 212, 277–281) N-acetyl-neuraminic acid (1) (15.0 g, Chemica Alta Ltd., Edmonton, Alberta, Canada) and acid resin (15.0 g, AG® 50 W-X2, 100–200 mesh, washed with methanol and acetonitrile, BioRad, Richmond, Calif., USA) in anhydrous methanol (350 mL) were stirred at room temperature for 18 h. The resin was then filtered and the filtrate was evaporated to dryness and the residue was dissolved in pyridine (100 mL) and acetic anhydride (50 mL). After 20 h, the reaction mixture was poured over crushed ice and the product was extracted with dichloromethane. The organic layer was separated and washed with ice-cold 0.5M hydrochloric acid and this procedure was repeated till the aqueous phased was acidic. The organic layer was then washed with saturated sodium bicarbonate solution, dried over anhydrous magnesium sulfate, filtered and evaporated to obtained a foamy residue (21.6 g).

EXAMPLE 2

Methyl 7,8,9-Tri-O-acetyl-2,3-didehydro-2,3,5-trideoxy-4',5'-dihydro-2'-methyloxazolo[5,4-d]-D-glycero-D-talo-2-nonulopyranosidonate 3: Compound 3 was prepared by according to the literature method (Schreiner, E.; Zbiral, E.; Kleineidam, R. G.; Schauer, R. *Liebigs Ann. Chem.* (1991) 129–134). Compound 2 (14.4 g) in anhydrous acetonitrile (150 mL) containing trimethylsilyl trifluromethanesulfonate (13.0 g, Aldrich Chemical Co. Inc., Milwaukee, Wis.) was heated to 50° C for 3 h. The reaction mixture was cooled in ice-bath and stirred with anhydrous sodium carbonate (13.0 g) for 30 min. The reaction mixture was then filtered and concentrated to a dry residue, which was redissolved in $CH_2Cl_2$ and washed with aqueous sodium bicarbonate. The organic layer was dried over $MgSO_4$, filtered and evaporated to obtained a syrupy material (9.0 g). The structure of product 3 was confirmed by comparison with the published NMR data (Schreiner et al.).

EXAMPLE 3

Methyl (5-acetamido-7,8,9-tri-O-acetyl-2,6-anhydro-4-azido-3,4,5-trideoxy-D-glycero-D-galacto-non-2en)onate 4: Compound 4 was prepared according to the published procedure (von Itzstein, M.; Jin, B.; Wu, W. Y.; Chandler, M. *Carbohydr. Res.* (1993) 244, 181–185). Trimethylsilyl azide (7.65 mL, Aldrich Chemical Co., Milwaukee, Wis.) was added to a solution of compound 3 (5.7 g) in t-butanol (50 mL) and heated at 80° C. for 4 h. The reaction mixture was concentrated to dryness and the residue was dissolved in dichloromethane and washed with water and saturated sodium chloride solution. The solvent was then evaporated and the product was purified by chromatography using ethylacetate-hexane-ethanol (10:15:1) as eluant. The yield of the product was 5.0 g. The structure of 4 was confirmed by comparison with the published NMR data (von Itzstein et al.).

EXAMPLE 4

Methyl (5-acetamido-7,8,9-tri-O-acetyl-4-azido-3,4,5-trideoxy-D-glycero-D-galacto-nonulopyranosylchloride)onate 5: Anhydrous HCl gas (Aldrich Chemical Co., Milwaukee, Wis.) was bubbled through an ice-cold solution of 4 (2.0 g) in acetonitrile (50 mL) containing 4 Å molecular sieves (5.0 g) and lithium chloride (1.0 g) for 20 min. The solution was then stirred at ambient temperature for 4 d. The reaction mixture was cooled in ace-bath and the HCl gas bubbled for additional 10 min and the reaction was continued for 2 more d. The reaction mixture was then evaporated under reduced pressure to dryness and the residue was extracted with dichloromethane. The dichloromethane solution was washed with ice-cold water (2×) and then with saturated sodium bicarbonate solution, dried over anhydrous $MgSO_4$, filtered and concentrated to a dry residue (1.6 g). $^1$H-NMR of the crude product showed that the product has grater than 85% of compound 5 and the about 10% of starting material 4. $^1$H-NMR ($CDCl_3$) ∂: 5.63 (d, 1H, J=9.6 Hz, NH), 5.46 (dd, 1H, J=2.8, 7.2 Hz, H-7), 5.19 (m, 1H, H-8), 4.52 (dd, J=2.8, 11.0 Hz, H-6), 4.40 (dd, J=3.2, 12.8 Hz, H-9a), 4.26 (m, 1H, H-4), 4.10 (dd, J=5.6, 12.8 Hz, H-9b), 3.88 (s, C)$CH_3$), 3.76 (m, H-5), 2.79 (dd, J=4.8, 14.3 Hz, H-3eq), 2.14, 2.07, 2.06 and 2.03 (4×s, $CH_3COO$—).

EXAMPLE 5

6,7-Dideoxy-1,2;3,4-di-O-isopropylidene-6-thio-α-D-galactoheptopyranose 6: This was prepared as described in the patent application U.S. Ser. No. 07/904,233. To a solution of 7-deoxy-1,2;3,4=di-O-isopropylidine-α-D-glyco-D-galactoheptopyranose (prepared as in Lemieux et al., Can. J. Chem. 60, 81–86(1981)) (7.8 g) in $CH_2Cl_2$ (150 mL) at 0° C., pyridine (10 mL) and trifluoromethanesulfonic anhydride (10.2 g) were added and the reaction mixture was stirred at 0° C. for 1 h. The reaction mixture was diluted with dichloromethane and washed with water, ice cold 1M hydrochloric acid and saturated sodium bicarbonate solution. The solvent was evaporated and the crude product was dissolved in DMF (150 mL) containing potassium thioacetate (5.5 g, Janssen Chimica, New Brunswick, N.J.) and stirred at room temperature for 18 h. The solvent was evaporated and the residue was dissolved in dichloromethane and washed with water, ice cold 1M hydrochloric acid and saturated sodium bicarbonate solution. Purification by chromatography on silica gel using ethyl acetate-hexane (1:12) afforded 6,7-dideoxy-1,2;3,4-di-O-isopropylidene-6-acetylthio-α-D-glycero-D-galactoheptopyranose (5.6 g).

$^1$H NMR ($CDCl_3$) ∂: 5.58 (d, H-1), 4.58 (dd, H-3), 4.37 (dd, H-4), 4.29 (dd, H-2), 3.88 (dd, H-5), 3.74 (m, H-6), 2.31 (s, S—Ac), 1.52, 1.45, 1.33 and 1.32 (isopropylidene methyls), 1.43 (d, H-7).

A portion of the above residue (4.6 g) was dissolved in dry methanol (40 mL) at 0° C. containing 30% ammonium hydroxide (4.6 mL) and dithiothreitol (2.8 g). After 16 h at 0° C., the solvent was evaporated and the residue was dissolved in $CH_2Cl_2$, dried with anhydrous $MgSO_4$, and concentrated. Purification of the product by chromatography on a column of silica gel (ethyl acetate-hexane=1:20) afforded the title product 6 (3.3 g). $[\alpha]_D^{25}$–59.8°±2°, (c 1.02, $CHCl_3$). $^1$H NMR ($CDCl_3$) ∂: 5.54 (d, H-1), 4.65–4.59 (m, 2H), 4.30 (dd, 1H), 3.45 (dd, 1H), 3.12 (m, H-6), 1.66 (d, SH), 1.4 (d, H-7), 1.53, 1.44, 1.35 and 1.33 (isopropylidene methyls). $^{13}$C NMR ($CDCl_3$) ∂: 109.1, 108.6, 96.8, 73.6, 71.1, 70.97, 70.4, 33.63, 26.0, 25.9, 24.9, 24.4, 21.7. Anal. Calcd for $C_{13}H_{22}O_5S$: C, 53.79; H, 7.58: Found: C, 53.90; H, 7.71.

EXAMPLE 6

Methyl 5-acetamido-7,8,9-tri-O-acetyl-4-azido-2-methylthio-3,4,5-trideoxy-α-D-glycero-D-galactononulopyranosylonate 7: Sodium thiomethoxide (1.13 g, 16.2 mmol, Aldrich Chemical Co., Milwaukee, Wis.) was added to a solution of compound 5 (1.6 g) in acetonitrile (20 mL) containing molecular sieves (4 Å, 1.0 g) and stirred under dry nitrogen atmosphere for 40 h. The reaction mixture was then concentrated to dryness, the residue suspended in dichloromethane and poured over ice-cold HCl. The organic layer was separated, washed with saturated sodium bicarbonate solution, dried over anhydrous magnesium sulfate and concentrated to a dry residue (1.4 g). $^1$H-NMR of the crude product confirmed the major component to be 7 along with minor amounts 4 that was present in the chloride 5. The purity of the crude material was found to be sufficient for subsequent glycosylation reactions. Analytically pure 7 was obtained by chromatography on a column of silica gel using ethylacetate-hexane-ethanol (10:15:1) as eluant. IR ($CHCl_3$) $cm^{-1}$: 2103 ($N_3$), 1742 (ester). $^1$H-NMR ($CDCl_3$) ∂: 5.60 (d, J=9.6 Hz, NH), 5.38 (m, 1H, H-8), 5.30 (dd, J=1.8, 9.0 Hz, H-7), 4.30 (dd, J=2.7, 12.2 Hz, H-9a), 4.17 (dd, J=4.6, 12.2 Hz, H-6b), 4.07 (dd, J=1.9, 10.6 Hz, H-6), 4.0 (m, 1H, H-4), 3.81 (s, 3H, $COOCH_3$), 3.30 (m, 1H, H-5), 2.75 (dd, 1H, J=4.6, 12.9 Hz, H-3eq), 2.16, 2.15, 2.10, 2.04 and 1.99 (5×s, 4×$CH_3COO$— and S—$CH_3$), 1.75 (dd, 1H, J=11.8, 12.9 Hz, H-3ax).

EXAMPLE 7

Methyl 5-acetamido-7,8,9-tri-O-acetyl-4-azido-2-methylthio-3,4,5-trideoxyα-D-glycero-D-galactononulopyranosylonate (2-S-6)-7-deoxy-1,2;3,4-di-O-isopropylidene-α-D-galactoheptopyranose 8: Sodium hydride (23 mg) was added to a cold solution (–20° C.) of 6 (290 mg) in anhydrous DMF (10 mL). After 5 min, a solution of crude 5 (492 mg) in DMF (5 mL) was added and the reaction mixture was stirred at –20° C. for 4 h. It was then evaporated to dryness under reduced pressure and the residue was extracted with dichloromethane and water and combined. The dichloromethane layer was separated and washed with ice-cold 0.5M HCl followed by saturated sodium bicarbonate solution. The mixture obtained after evaporation of the solvent was purified by chromatography on a column of silica gel using ethylacetate-hexane-ethanol (10:15:1) as eluant to get pure 8 (350 mg). $^1$H-NMR ($CDCl_3$) ∂: 5.57 (d, J=8.4 Hz, NH), 5.50 (d, 1H, J=4.9 Hz, H-1), 5.32 (m, 1H, H-8), 5.28 (dd, 1H, J=2.2, 8.4 Hz, H-7), 4.55 (dd, J=2.7, 8.0 Hz, H-3), 4.40–4.17 (3H, H-9'a,b, H-2, H-4), 4.13 (dd, 1H, H-6'), 4.00 (m, 1H, H-4'), 3.81 (s, 3H, $COOCH_3$), 3.49 (dd, J=1.9, 8.0 Hz, H-5), 3.38–3.18 (H-6, H-5'), 2.78 (dd, J=4.3, 12.5 Hz, H-3'eq), 2.16, 2.13, 2.06 and 1.98 (4×s, $CH_3COO$), 1.76 (t, 1H, J=12.4 Hz, H-3'ax), 1.48, 1.44, 1.32 and 1.31 (4 s, 4-isopropylidene methyls), 1.46 (d, H-7).

EXAMPLE 8

Methyl 5-acetamido-7,8,9-tri-O-acetyl-4-azido-3,4,5-trideoxy-D-glycero-D-galacto-nonulopyranosid)onate (2-6)-1,2;3,4-di-O-isopropylidene-(α-D-galactoheptopyranose 9:

Methylsulfenyl bromide (1M in 1,2-dichloroethane) was added to a solution of 7 (850 mg), 1,2;3,4-di-O-isopropylidene-α-D-galactopyranose (655 mg, Pfanstiehl Laboratories, Inc., Waukegan, Ill.), silver trifluromethane-sulfonate (518 mg) and powdered 3 Å molecular sieves (1.5 g) in acetonitrile-dichloromethane mixture (4:1, 25 mL) at −30° C. The reaction was subsequently stirred at −38° C. for 16 h. Saturated sodium bicarbonate solution (3 mL) was added and the reaction mixture was stirred at room temperature for 10 min. It was then filtered over Celite pad and the residue washed with dichloromethane. The filtrate was washed with saturated sodium bicarbonate solution, dried over anhydrous magnesium sulfate and concentrated to a dry residue. Purification of this product by chromatography on silica gel using ethylacetate-hexane-ethanol (10:15:1) gave the unreacted 1,2;3,4-di-O-isopropylidene-α-D-galactopyranose (400 mg), followed by pure 9 (216 mg) and a mixture of 9 (431 mg) contaminated to about 10% with the glycal 4. IR (CHCl$_3$) cm$^{-1}$: 2104 (N$_3$), 1747 (esters). $^1$H-NMR (CDCl$_3$) ∂: 5.51 (broad d, 2 H, J=4.3 Hz, H-1, NH), 5.39 (m, 1H, H-8'), 5.29 (dd, 1H, J=1.9, 8.2 Hz, H-7'), 4.59 (dd, 1H, J=H-3), 4.35–4.20 (m, H-2, H-4, H-9'a,b, H-6'), 3.95–3.75 (H-4', H-6, H-5, COOCH$_3$), 3.59 (m, H-6b?), 3.37 (m, H-5'), 2.67 (dd, 1H, J=4.4, 13.2 Hz, H-3'eq), 2.15, 2.13, 2.04 and 1.98 (4×s, 4×CH$_3$COO), 1.74 (t, 1H, J=13.3 Hz, H-3'ax), 1.53, 1.42, 1.32 and 1.31 (4×s, 4-isopropylidene methyls).

EXAMPLE 9

Sodium Salt of 5-acetamido-4-azido-3,4,5-trideoxy-D-glycero-D-galacto-nonulopyranosylonic acid (2-6)-α-D-galacto-pyranose 10:Sialoside 9 (90% pure, 425 mg) was dissolved in methanol (25 mL) followed by the addition of 0.5M sodium methoxide solution (0.2 mL). After 4 h, the reaction mixture was neutralized with acidic resin, evaporated to dryness, redissolved in water (5 mL) and purified by gel permeation chromatography on Bio gel P-2 to obtain pure methyl (5-acetamido-4-azido-3,4,5-trideoxy-D-glycero-D-galacto-nonulopyranosylonate (2-6)-1,2;3,4-di-O-isopropylidene-α-D-galacto-pyranose (270 mg). A portion of this (110 mg) was dissolved in 50% aqueous trifluoroacetic acid (10 mL) and kept at ice-bath temperature for 1 h and then at room temperature for 4 h. It was then evaporated to dryness, redissolved in water and applied on a column of Bio gel P2 (200–400 mesh, 1800 mL) equilibrated and eluted with water and the U.V. active (220 nm) fractions (7.5 mL, 119–126) were pooled and lyophilized (78 mg, methyl ester of 10). Hydrolysis of methyl ester (65 mg) with Chelex resin (760 mg) as described above gave the sialoside 10 (71 mg). $^{13}$C-NMR ∂: 176.0, 174.3, 101.4, 97.5, 93.4, 74.6, 74.0, 73.7, 72.9, 72.8, 70.4, 70.1, 69.9, 69.4, 69.2, 65.1, 64.9, 63.7, 60.6, 51.1, 38.3, 23.1.

EXAMPLE 10

Sodium Salt of 4,5-diacetamido-3,4,5-trideoxy-D-glycero-D-galacto-nonulopyranosylonic acid (2-6)-α-D-galacto-pyranose 11: Compound 10 (162 mg) was dissolved in methanol (15 mL) containing 10% Pd—C (48 mg) and left under hydrogen atmosphere for 18 h. It was then filtered over Celite pad, concentrated to a dry residue, redissolved in CH$_2$Cl$_2$ (15 mL) containing pyridine (1 mL) and acetic anhydride (0.5 mL). After 15 min, methanol (0.5 mL) was added and the reaction mixture was diluted with CH$_2$Cl$_2$ and washed with water, ice cold hydrochloric acid and saturated sodium bicarbonate solution. The residue from this was de-O-acetylated with 0.5M sodium methoxide in methanol, neutralized with acidic resin, concentrated and the residue from this was dissolved in 50% aqueous CF$_3$COOH and left in ice-bath temperature for 16 h. It was then concentrated to a dry residue, redissolved in water and applied on a column of Bio gel P-2 as described to obtain the methyl ester of 10 (75 mg). A portion (65 mg) of this was hydrolyzed with Chelex resin (650 mg) to obtain 10 (74 mg). $^{13}$C NMR ∂: 175.0, 174.1, 173.7, 100.7, 96.8, 92.7, 73.9, 73.6, 73.5, 73.0, 72.1, 69.7, 69.3, 69.2, 68.6, 64.3, 64.1, 63.0, 50.2, 48.8, 37.9, 22.2.

EXAMPLE 11

Sodium Salt of 5-acetamido-4-amino-3,4,5-trideoxy-D-glycero-D-galacto-nonulopyranosylonic acid (2-6)-α-D-galacto-pyranose 12: Compound 10 (26 mg) was dissolved in 90% aqueous ethanol (15 mL) containing 10% Pd—C (20 mg) and left under hydrogen atmosphere for 16 h. It was then filtered over Celite pad, concentrated to a dry residue, redissolved in water and lyophilized (12 mg). The structure was confirmed by $^1$H NMR.

EXAMPLE 12

Sodium Salt of 5-acetamido-4-azido-2-thio-3,4,5-trideoxy-D-glycero-D-galacto-nonulopyranosylonic acid(2-S-6)-7-deoxy-α,β-D-glycero-D-galacto-heptopyranose 13: Sialoside 8 (370 mg) was dissolved in anhydrous methanol (15 mL) followed by the addition of 0.5M sodium methoxide solution (0.2 mL). After 2 h, the solution was neutralized with H+resin, filtered and evaporated to give methyl (5-acetamido-4-azido-2-thio-3,4,5-trideoxy-D-glycero-D-galacto-nonulopyranosyl)-onate(2-S-6)-7-deoxy-1,2;3,4-di-O-isopropylidene-α,-D-glycero-D-galacto-heptopyranose 39. The residue was dissolved in 50% aqueous CF$_3$COOH (10 mL) and left at room temperature for 4 h and then for 16 h at 4° C. The solution was evaporated to dryness and purified on a column of Bio gel P-2 (200–400 mesh, 1800 mL). This gave the methyl ester of 13 (196 mg). Hydrolysis of the methyl ester (185 mg)was carried out with Chelex resin (1.0 g, 40° C., 3 d) to obtain 13 (185 mg). The structure was confirmed by $^1$H NMR.

EXAMPLE 13

Sodium Salt of 5-acetamido-4-amino-2-thio-3,4,5-trideoxy-D-glycero-D-galacto-nonulopyranosylonic acid(2-S-6)-7-deoxy-α,β-D-glycero-D-galacto-heptopyranose 14: Compound 13 (25 mg) was dissolved in 90% aqueous ethanol (10 mL) containing 20% Pd(OH)$_2$—C (25 mg) and stirred under hydrogen atmosphere for 90 min. The reaction mixture was concentrated to dryness, redissolved in water and applied on a column of Sephadex G-15, equilibrated and eluted with water. The fractions containing the products, as evidenced by U.V. absorption at 220 nm, were pooled and lyophilized (12 mg). $^{13}$C-NMR ∂: 175.4, 173.8, 97.1, 92.6, 87.0, 86.9, 77.3, 75.1, 73.3, 72.5, 72.3, 72.2, 72.1, 69.9, 69.5, 69.1, 68.6, 68.0, 67.9, 62.7, 51.1, 48.0, 39.9, 39.6, 37.4, 22.4, 20.6, 20.4.

EXAMPLE 14

Hydrolysis of sialidase substrates as determined by colorimetric neuraminidase Assays The activity of neuraminidase was measured with a radiolabeled substrate. For the radiolabeled assay the inhibition constants (Ki) for 12 and 14 were determined by incubating (37° C.) a solution of A at four different concentrations (approx. at 0.5, 1, 2 and 4 times the Km of A for the enzyme), with the neuraminidase, in the presence (at three inhibitor concentrations) or absence of the inhibitors, for 20 or 30 min. This was followed by estimating the amount of free LacNac liberated. The buffer used in these neuraminidase reactions was 100 mM NaOAc- 5 mM $Na_2HPO_4$ (pH 5.5). The 4 concentrations of A used in these assays for influenza A neuraminidase for both 12 1nd 14 were 1.0, 2.0, 4.0 and 8.0 mM. The inhibitor concentrations were 0.07, 0.14 and 0.28 mM.

The neuraminidase concentration was 53 ug of influenza A virus in 60 uL of total reaction volume. After the reaction, the reaction mixture was diluted with deionized water (1 mL), and passed through a column of Dowex resin (phosphate form, 200–400 mesh, 2 mL of a 1 g/mL suspension of the resin in deionized water). The column was further eluted with deionized water (2 mL). Under these conditions, only the free LacNAc eluted. The eluant was diluted with Scintillation fluid (10 mL), Formula 989, NEN, MA) and the radioactivity was measured for 2 or 5 min with a Liquid Scintillation counter. From the Lineweaver-Burk plots for the hydrolysis of A the inhibition constant Ki was calculated according to methods known in the art.

Figure 2B:
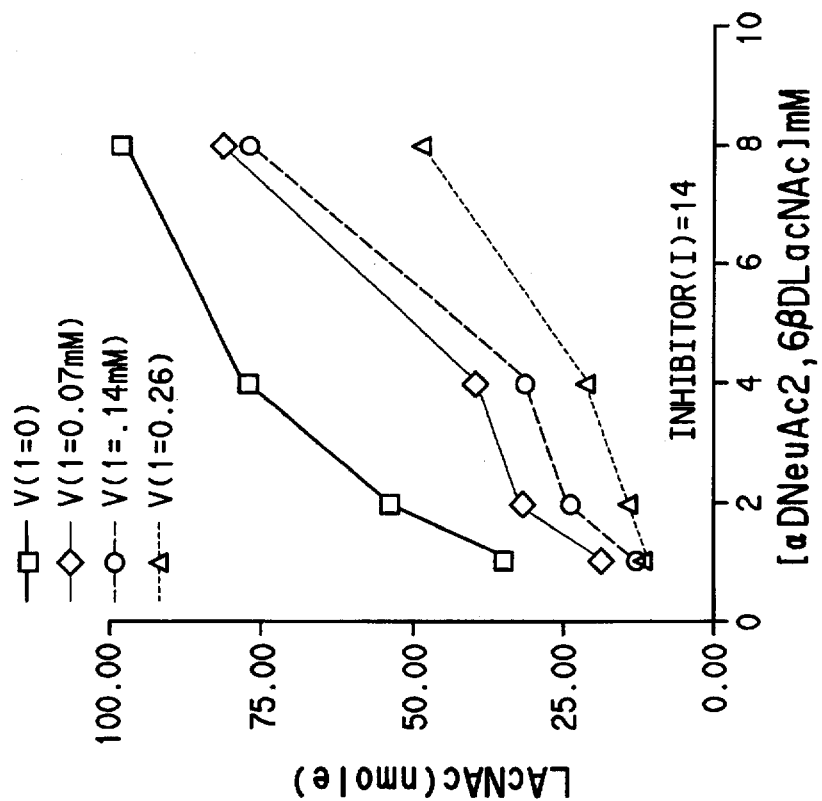
Figure 2A:
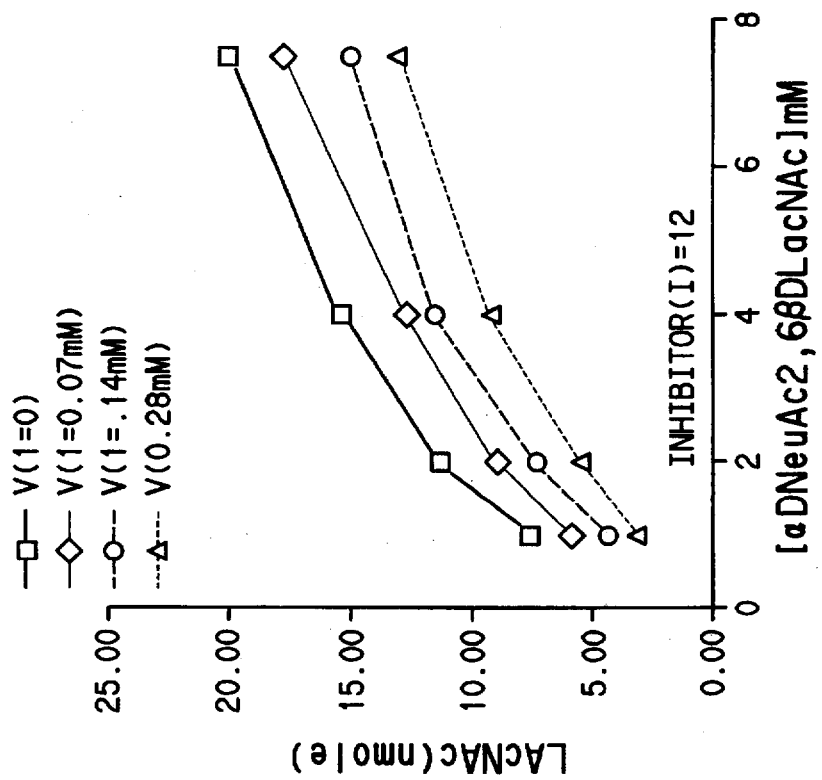

FIG. 2A shows the influenza virus neuraminidase hydrolysis of A in the absence (I=0) and in the presence of 12 at three concentrations. FIG. 2B shows a similar plot for 14. It is evident from these results that both 12 and 14 were good inhibitors of influenza neuraminidase, (Ki=100 and 51 mM, respectively.

What is claimed:

1. A process for the hydrochlorination of 4-azido-2,3-dehydrosialic acids or 4-deoxy-2,3-dehydrosialic acids (I) to the corresponding 4-azido-2-chlorosialic acids or 4-deoxy-2-chlorosialic acids (II) according to the equation

I → II where $R^1$ is $C_1$ to $C_{20}$ alkyl;
$R^2$ is azido or hydrogen;
$R^3$ is H or a $C_1$ to $C_{20}$ hydrocarbyl or substituted hydrocarbyl; and
$R^4$ is acyl containing from 1 to 8 carbon atoms, or a $C_1$ to $C_{20}$ alkyl;

which process comprises contacting under substantially anhydrous conditions the 4-azido-2,3-dehydrosialic acid or 4-deoxy-2,3-dehydrosialic acid with anhydrous hydrogen chloride in the presence of a polar aprotic solvent or a organic carboxylic acid solvent.

2. The process of claim 1 further comprising performing the reaction in the presence of lithium chloride.

3. The 4-azido-2-chlorosialic acids or 4-deoxy-2-chlorosialic acids of the structure II product of claim 1.

4. A compound of the structure

III where

X is oxygen, sulfur, $CR^9R^{10}$, or $NR^{11}$, $R^1$ is H, $C_1$–$C_{20}$ alkyl, a mono, di or polyvalent cation of an alkali metal, alkaline earth metal or transition metal, or an ammonium or substituted ammonium ion;

$R^2$ is azido, acylamino, where the acyl group contains from 1 to 8 carbon atoms, amino, hydrogen or guanidino;

$R^3$ is H or a $C_1$ to $C_{20}$ hydrocarbyl or substituted hydrocarbyl;

$R^4$ is H, acyl containing from 1 to 8 carbon carbon atoms, or a $C_1$ to $C_{20}$ alkyl;

$R^5$ is H, a $C_1$ to $C_{20}$ hydrocarbyl or substituted hydrocarbyl;

$R^6$ and $R^{6'}$ are H, OH, a $C_1$ to $C_{20}$ alkoxy or substituted alkoxy, a mono, di or oligosaccharide, or an alkylideneoxy taken together with $R^{7'}$ when $R^{7'}$ is not H; provided that one of $R^6$ and $R^{6'}$ must be H but $R^6$ and $R^{6'}$ may not both be H; and $R^7$ and $R^{7'}$ are H, acyl containing from 1 to 8 carbon atoms, or a $C_1$ to $C_{20}$ alkyl, aryl, or alkylidene taken together with an adjacent $R^6$, $R^{6'}$ $R^7$ or $R^{7'}$;

where $R^9$, $R^{10}$ and $R^{11}$ are independently H or a $C_1$–$C_{20}$ hydrocarbyl or substituted hydrocarbyl.

5. A compound of the structure

IV where $R^1$ is H, $C_1$–$C_{20}$ alkyl, a mono, di or polyvalent cation of an alkali metal, alkaline earth metal or transition metal, or an ammonium or substituted ammonium ion;

$R^2$ is azido, acylamino, where the acyl group contains from 1 to 8 carbon atoms, amino, guanidino, or hydrogen;

$R^3$ is H or $C_1$ to $C_{20}$ hydrocarbyl or substituted hydrocarbyl;

$R^4$ is H, acyl containing from 1 to 8 carbon atoms or a $C_1$ to $C_{20}$ alkyl;

$R^8$ is $C_1$ to $C_{20}$ hydrocarbyl or substituted hydrocarbyl, acyl containing from 1 to 8 carbon atoms;

$R^9$, $R^{10}$ and $R^{11}$ are independently H or a $C_1$–$C_{20}$ hydrocarbyl or substituted hydrocarbyl; and X is oxygen, sulfur, $CR^9R^{10}$ or $NR^{11}$.

6. A method for inhibiting sialidase activity comprising contacting sialidase with a compound of the formula III

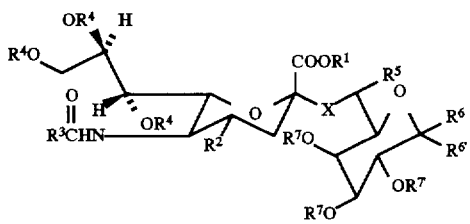

III

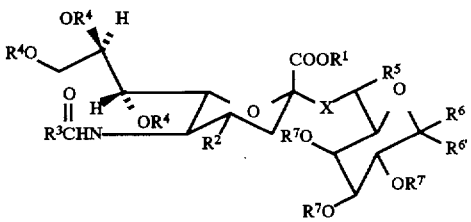

III where

X is oxygen, sulfur, $CR_9R^{10}$, or $NR_{11}$;

$R^1$ is H, a mono, di or polyvalent cation of an alkali metal, alkaline earth metal or transition metal, or an ammonium or substituted ammonium ion;

$R^2$ is amino or a guanidino;

$R^3$ is H or $C_1$ to $C_{20}$ hydrocarbyl or substituted hydrocarbyl;

$R^4$ is H;

$R^5$ is a H, $C_1$ to $C_{20}$ hydrocarbyl or substituted hydrocarbyl;

$R^6$ and $R^{6'}$ are H, OH, a $C_1$ to $C_{20}$ alkoxy or substituted alkoxy, a mono, di or oligosaccharide, or an alkylideneoxy taken together with $R^{7'}$ when $R^{7'}$ is not H; provided that one of $R^6$ and $R^{6'}$ must be H but $R^6$ and $R^{6'}$ may not both be H; and $R^7$ and $R^{7'}$ are H or alkylidene taken together with an adjacent $R^6$, $R^{6'}$, $R^7$ or $R_7'$;

where $R^9$, $R^{10}$ and $R^{11}$ are independently H or a $C_1-C_{20}$ hydrocarbyl or substituted hydrocarbyl.

7. The compound of claim 4 having sialidase resistance and having the structure where X is oxygen, sulfur, $CR^9R^{10}$, or $NR^{11}$;

$R^1$ is H, $C_1-C_{20}$ alkyl, a mono, di or polyvalent cation of an alkali metal, alkaline earth metal or transition metal, or an ammonium or substituted ammonium ion:

$R^2$ is amino or a guanidino;

$R^3$ is H or $C_1$ to $C_{20}$ hydrocarbyl or substituted hydrocarbyl:

$R^4$ is H;

$R^5$ is a H, $C_1$ to $C_{20}$ hydrocarbyl or substituted hydrocarbyl:

$R^6$ and $R^{6'}$ are H, OH, a $C_1$ to $C_{20}$ alkoxy or substituted alkoxy, a mono, di or oligosaccharide, or an alkylideneoxy taken together with $R^{7'}$ when $R^{7'}$ is not H; provided that one of $R^6$ and $R^{6'}$ must be H but $R^6$ and $R^{6'}$ may not both be H; and $R^7$ and $R^{7'}$ are H or alkylidene taken together with an adjacent $R^6$, $R^{6'}$, $R^7$ or $R^{7'}$;

where $R^9$, $R^{10}$ and $R^{11}$ are independently H or a $C_1-C_{20}$ hydrocarbyl or substituted hydrocarbyl.

* * * * *